United States Patent
Boebel et al.

(10) Patent No.: US 6,458,077 B1
(45) Date of Patent: Oct. 1, 2002

(54) MEDICAL INSTRUMENT, IN PARTICULAR A RECTOSCOPE

(75) Inventors: Manfred Boebel, Neulingen; Dieter Metsch, Kraichtal, both of (DE); Jose M. Ramirez Rodriguez, Zaragoza (ES); Gerhard Fritz Buess, Tuebingen (DE)

(73) Assignee: Richard Wolf GmbH, Knittlingen (DE)

( * ) Notice: Subject to any disclaimer, the term of this patent is extended or adjusted under 35 U.S.C. 154(b) by 206 days.

(21) Appl. No.: 09/628,573

(22) Filed: Jul. 31, 2000

(30) Foreign Application Priority Data

Jul. 29, 1999 (DE) .......................... 199 35 725

(51) Int. Cl.⁷ ............................................... A61B 1/018
(52) U.S. Cl. ...................................... 600/154; 600/114
(58) Field of Search .................. 600/105, 114, 600/154; 604/264, 167.01, 167.02, 167.03, 167.04

(56) References Cited

U.S. PATENT DOCUMENTS

| | | | |
|---|---|---|---|
| 3,583,710 A | | 6/1971 | Burelle |
| 4,112,932 A | | 9/1978 | Chiulli |
| 4,177,814 A | | 12/1979 | Knepshield et al. |
| 4,538,594 A | * | 9/1985 | Boebel et al. ............... 600/102 |
| 4,776,845 A | * | 10/1988 | Davis ........................ 600/114 |
| 5,338,307 A | | 8/1994 | Stephens et al. |
| 5,385,560 A | | 1/1995 | Wulf |
| 5,569,205 A | | 10/1996 | Hart et al. |
| 5,752,938 A | | 5/1998 | Flatland et al. |
| 5,913,870 A | | 6/1999 | DeFonzo et al. |
| 6,117,070 A | * | 9/2000 | Akiba ........................ 600/154 |
| 6,142,931 A | * | 11/2000 | Kaji ........................... 600/102 |
| 6,162,196 A | * | 12/2000 | Hart et al. ................ 604/167.02 |

FOREIGN PATENT DOCUMENTS

| | | |
|---|---|---|
| DE | 33 19 049 | 5/1984 |
| DE | 42 34 452 | 4/1994 |
| DE | 694 05 798 | 2/1998 |
| EP | 153 190 | 8/1985 |
| GB | 2 130 889 | 6/1984 |
| WO | WO92/19146 | 11/1992 |

* cited by examiner

Primary Examiner—John P. Leubecker
(74) Attorney, Agent, or Firm—Cohen, Pontani, Lieberman & Pavane

(57) ABSTRACT

The instrument has a working insert which may be inserted into a coupling housing sitting on the proximal side on an instrument shank and is releasably connectable to said housing and which includes a seal, carried by a carrier, which has at least one elastic socket for the sealed leading-through of auxiliary instruments and which seals a first axial passage formed in the carrier with respect to the coupling housing. The seal consists of a base body which is located in a holder and which with each socket forms a one-piece component of elastic material, and the holder includes an arrangement for the releasable connection to the carrier.

17 Claims, 6 Drawing Sheets

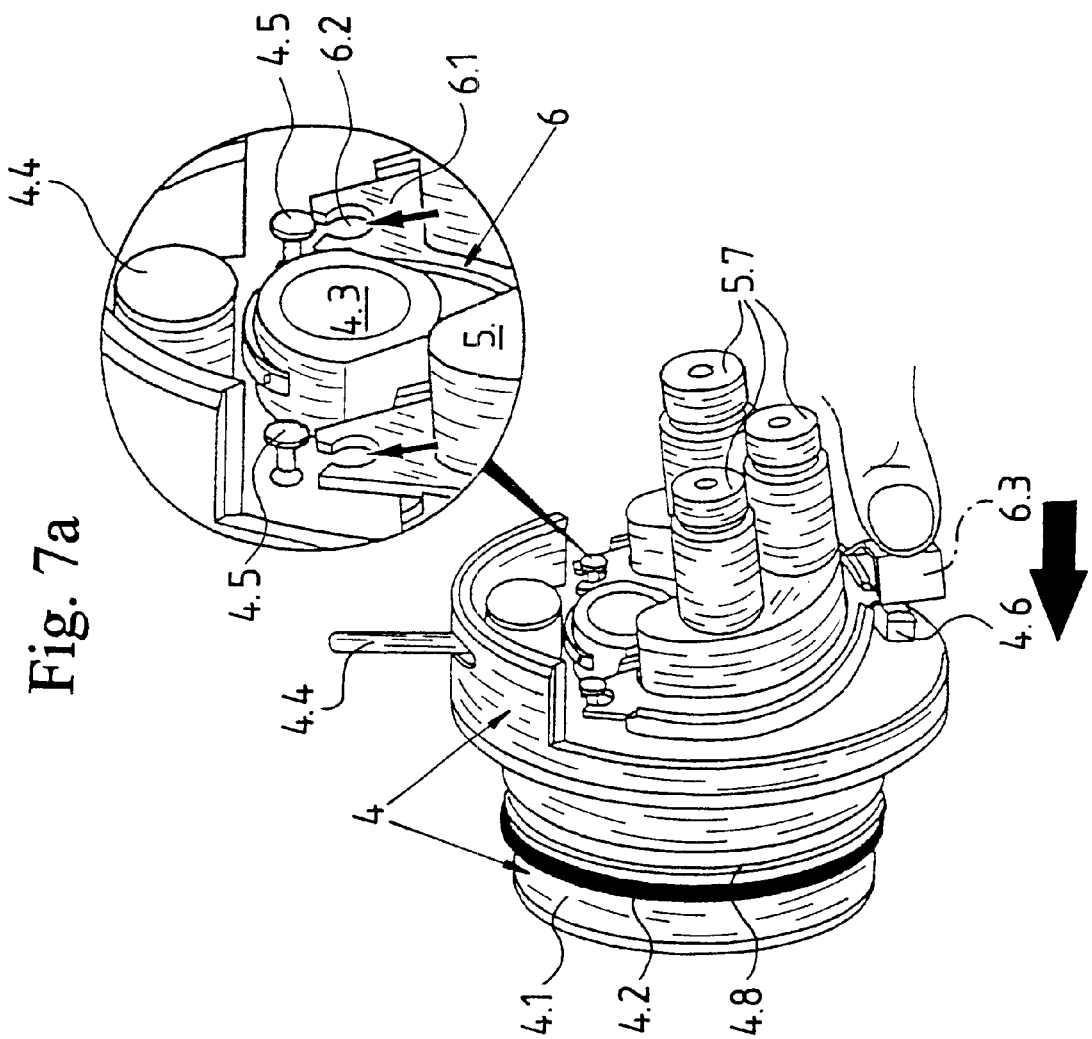

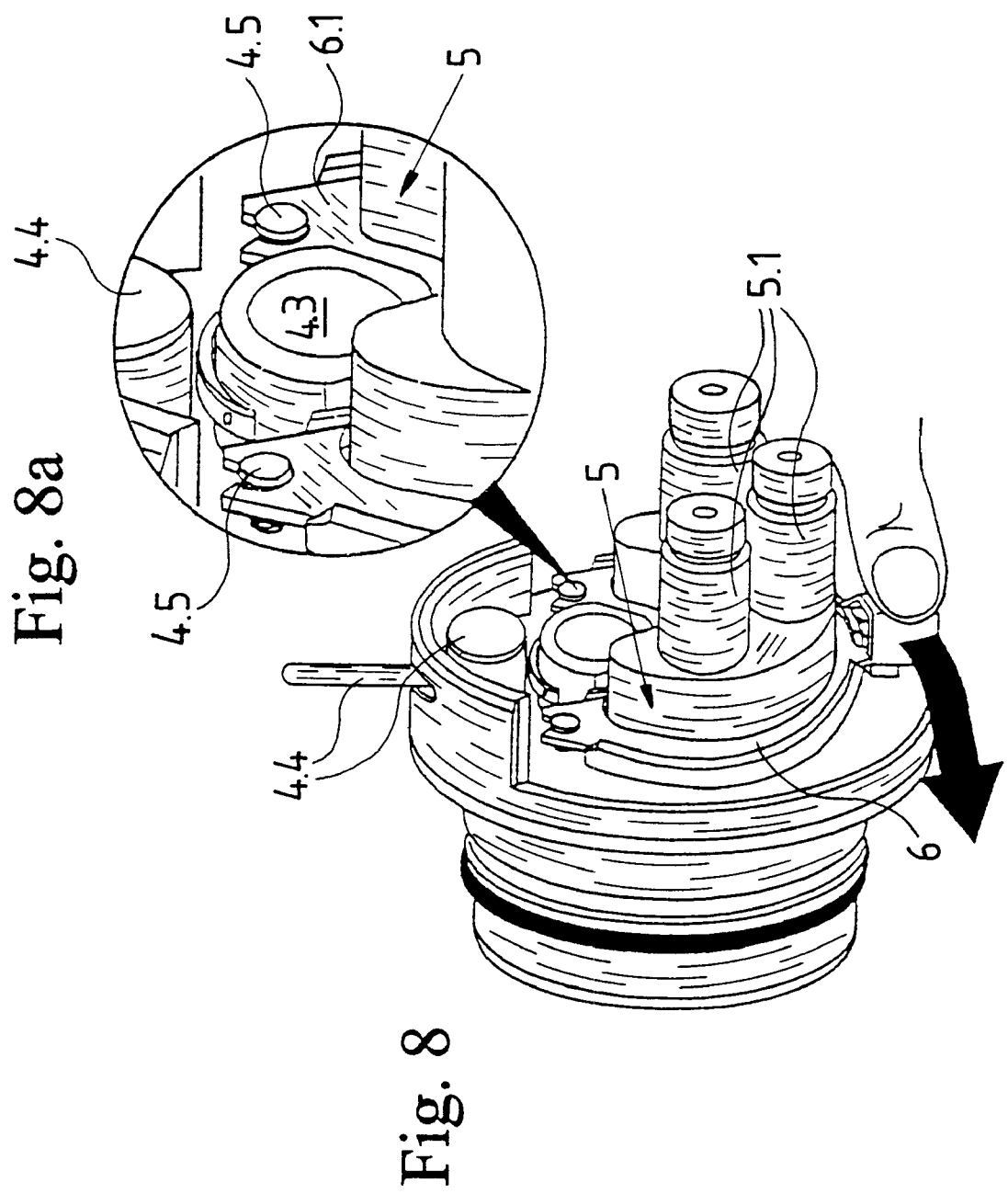

MEDICAL INSTRUMENT, IN PARTICULAR A RECTOSCOPE

BACKGROUND OF THE INVENTION

The invention relates to a medical instrument, in particular a rectoscope, with a working insert which may be inserted into a coupling housing sitting on the proximal side on an instrument shank and is releasably connectable to said housing and which comprises a seal, carried by a carrier, which has at least one elastic socket for the sealed leading-through of auxiliary instruments and which seals a first axial passage formed in the carrier with respect to the coupling housing. Such a medical instrument is known from DE 33 19 049 C2.

With transanal endoscopic microsurgery (TEM) a maximum freedom of movement of TEM and auxiliary instruments introduced through the working insert into the instrument shank, a quicker and problem-reduced change of defect sealing elements as well as a quick removal possibility of resected tissue parts is demanded. Since the proximal ends of the three individual accesses formed in the working insert of the known endoscope in each case have a bulge-shaped thickening and over these bulge-shaped thickening elastic sealing sockets are pushed, by way of the restricted conditions problems with a TEM operation may occur. Furthermore with the known rectoscope the action radius and the movement freedom of the TEM instruments are restricted by tube connections. For removing operation preparations furthermore the complete working insert with the applied optics must be removed.

BRIEF SUMMARY OF THE INVENTION

It is the object of the invention to provide a medical instrument according to the known type, in particular a rectoscope, which creates an access suitable for the extensive free movability of several TEM instruments and has a working insert with a large-lumened as possible instrument passage and with a quickly exchangeable and inexpensively manufacturable sealing element, suitable as a wearing part, on the instrument passage on which the sealing element can be simply locked and unlocked.

Proceeding from a medical instrument according to the known type and the type previously mentioned this object according to the invention is achieved in that the seal consists of a base body which is located in a holder and which with each socket forms a one-piece component of elastic material, and that the holder comprises means for the releasable connection to the carrier.

By way of the one-piece formation of the base body with the sockets the seal may excellently fulfill its sealing functions and it may, since it may be easily releasably fastened on the carrier, be advantageously manufactured as an inexpensive single-use or disposable article.

By way of the fact that the holder of the seal comprises means for the simply releasable connection to the carrier, the complete sealing element may be simply inserted into the carrier and again be released therefrom. If one unites the seal with the holder on manufacture to a one-piece component then the handling, i.e. the fastening and the removal of the seal with the holder onto and out of the carrier is simplified even further. The seal may, corresponding to the respective application purpose, be made available in differing variants which may only have a single or several elastic sockets for introducing several auxiliary instruments.

The first passage in the carrier preferably has a large-lumened crescent-shaped contour which matches with a distal-side attachment on the base body of the seal, and the socket or sockets projecting proximally from the base body end in a passage of the base body in the region of the attachment. With this embodiment form the holder encompassing the base body is likewise essentially crescent-shaped and formed in the manner of a bow. This bow has an axial opening whose contour is likewise crescent-shaped and thus corresponds to the crescent-shaped outer contour of the base body so that the holder may encompass the base body with a positive fit in the region of its attachment.

By way of its crescent-shaped contour the first passage offers a relatively large opening in the carrier, through which the used auxiliary instruments in the body cavity may be very well manipulated.

The attachment may, where it is enclosed by the holder, comprise an annular shoulder on which the holder lies. This annular shoulder may on its proximal-side shoulder surface comprise a crescent-shaped deepening which here accommodates the holder with a positive fit.

Preferably the two bow ends of the holder in each case comprise a recess such that the have a fork shape, by which means the holder with the bow ends may be easily releasably fastened with a positive and non-positive fit to fastening pegs projecting proximally from the end-side face of the carrier and tapering conically in the distal direction. The use of the bow-shaped holder with its fork-shaped formed ends simplifies the fastening and the simple releasability of the seal on the carrier since the fork-shaped ends only need to be suspended into the fastening peg and at the opposite side pressed against the end-side face of the carrier.

A second passage in the carrier serving for introducing an optic is provided at a distance from the first crescent-shaped passage such that the second passage lies free of the seal. By way of the crescent contour of the first passage in the carrier and the corresponding crescent shape of the seal and of the holder encompassing the seal thus the second passage in spite of the large-lumened first passage lies relatively tightly on the longitudinal axis of the medical instrument.

By way of the restoring force of the elastic material of the annular shoulder, of the seal, pressed against the proximal-side surface of the carrier and by way of the centering effect of the mentioned tapering of the fastening peg, a secure and also gas and fluid tight fastening of the seal on the carrier is achieved. On account of the relatively high friction which the elastic material from which the seal is manufactured comprises, the security of the fastening of the seal on the carrier is additionally increased and a lateral displacement of the seal on the carrier and a reduction of the sealing function is effectively prevented.

BRIEF DESCRIPTION OF THE DRAWINGS

In the subsequent description a particularly advantageous embodiment form of a medical instrument according to the invention is explained in more detail by way of example of a rectoscope with reference to the drawing figures.

FIGS. 7 and 7a show in each case and in an enlarged detailed representation the seal, before it is finally inserted into the carrier with the help of the holder, and connected thereto and FIGS. 8 and 8*a* show in each case perspectively and in an enlarged detailed representation the seal fastened on the carrier directly before its final fixation.

DETAILED DESCRIPTION OF THE INVENTION

Figure 1:
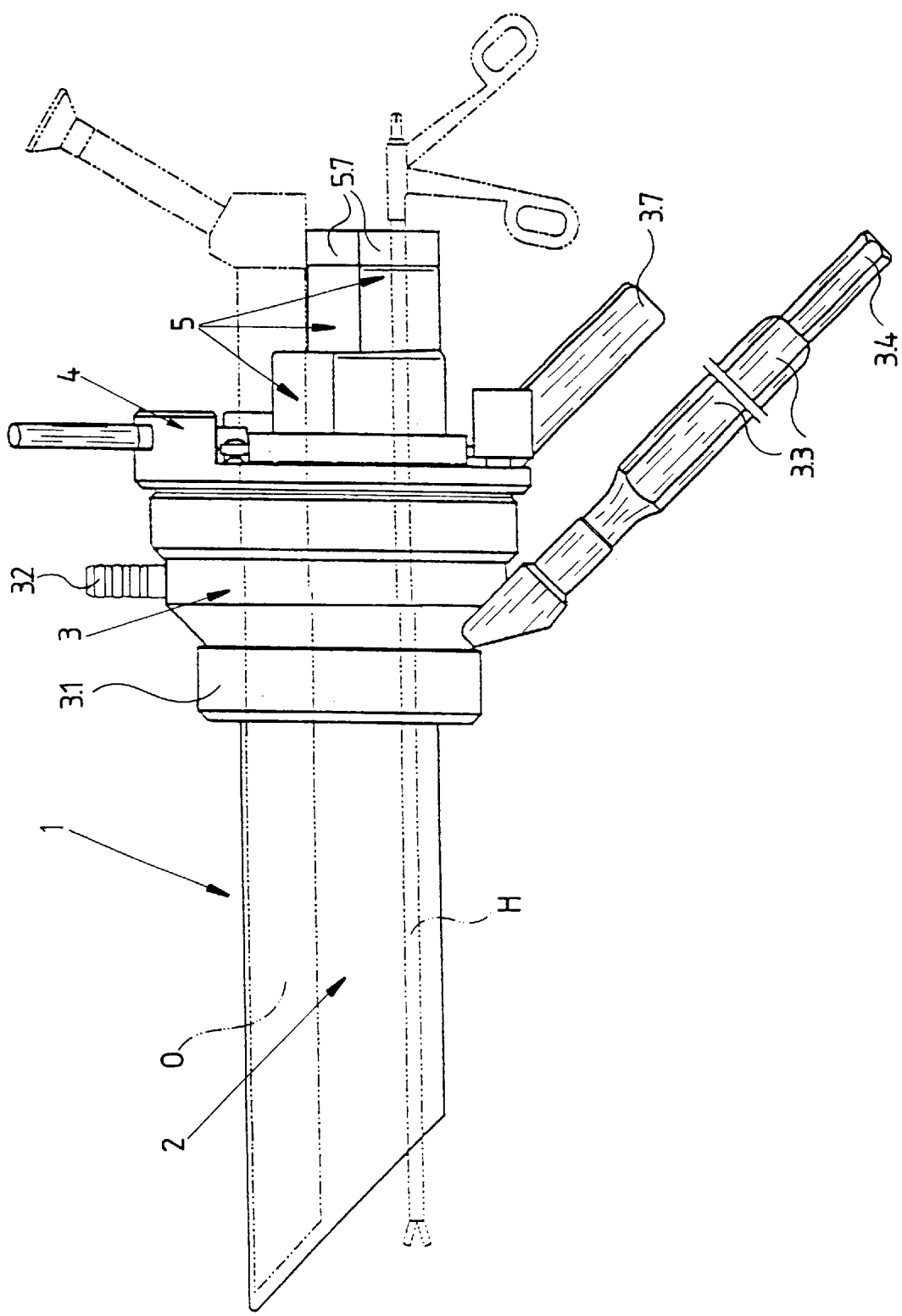
FIG. 1 shows schematically in a lateral view a rectoscope.

The medical instrument 1 according to FIG. 1 is a rectoscope and consists essentially of five main components, specifically of the shank 2, the coupling housing 3, the carrier 4 and the sealing element 5 which is releasably fixed thereon and which together with the carrier 4 forms the working insert. The shank 2 is exchangeable and is thus adaptably arranged, corresponding to the respective application purpose, at the distal end of the coupling housing 3 and fastened with a screw or bajonette ring 3.1.

For the supply and removal of the gas expanding the body cavity, on the coupling housing 3 there is arranged a radially projecting connection piece 3.2 and for holding the instrument there is located a handle 3.3 arranged at an angle to the instrument longitudinal axis, on whose lower end there is arranged a fastening element 3.4 for the accommodation in a (non-shown) holding arm.

Figure 3:
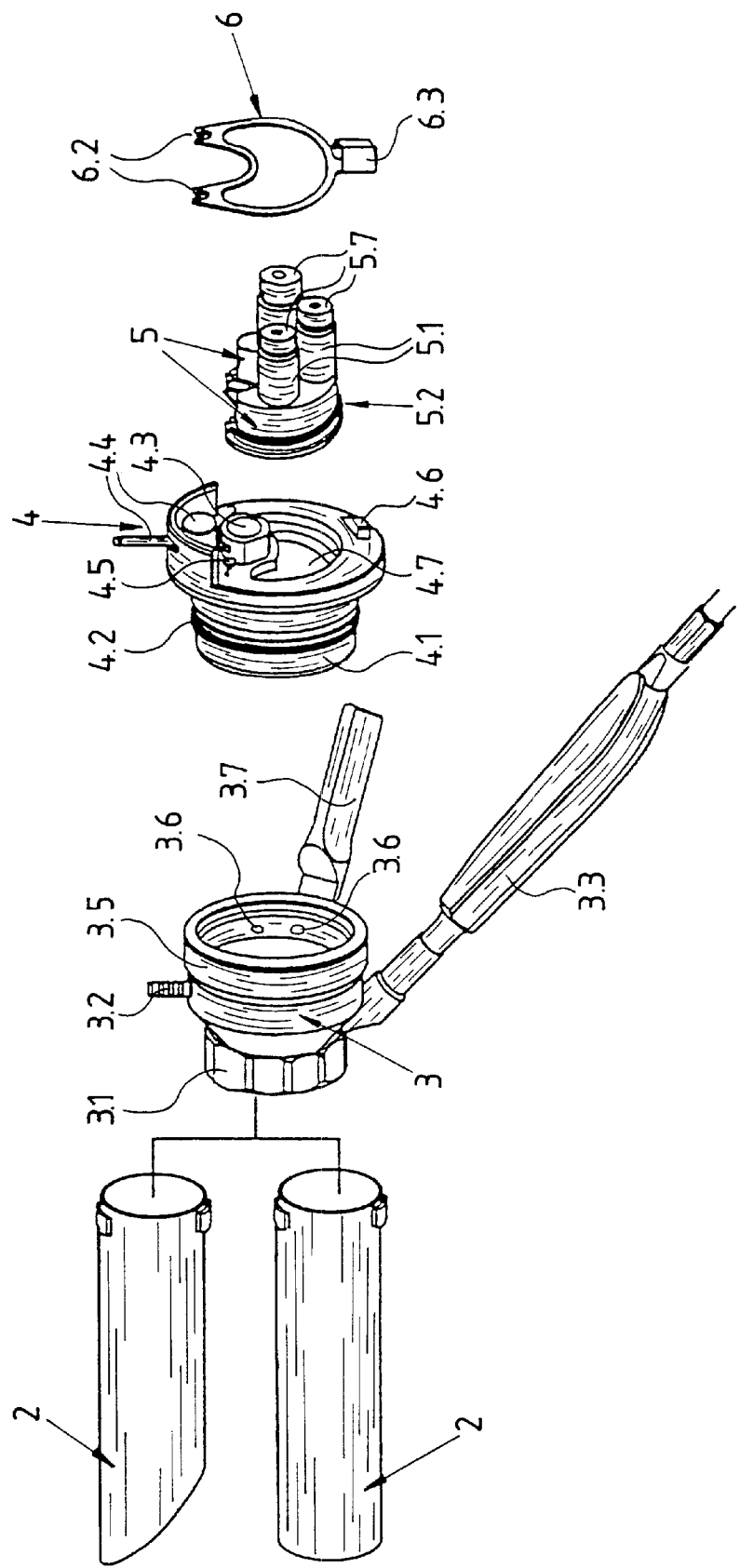
FIG. 3 shows in each case perspectively the five main components of the medical instrument, shown in FIG. 1, in the form of an exploded representation.

The carrier 4 from the proximal side is insertable into the open end, of the coupling housing 3, which cannot be recognized in FIG. 1, but in FIG. 3 and is releasably connectable to a closure ring 3.5 which acts on blocking balls 3.6. The closure ring 3.5 may be rotated on a handle 3.7 about the proximal end of the coupling housing 3.

Into the thus formed instrument from the proximal side there may be inserted at least one auxiliary instrument, drawn dashed, and an optic O likewise drawn dashed. With this the working insert consisting of the carrier 4 and the seal 5 serves the support and the sealed leading-through of the auxiliary instrument or instruments as well as the optic, as this will be described in more detail further below.

Figure 2:
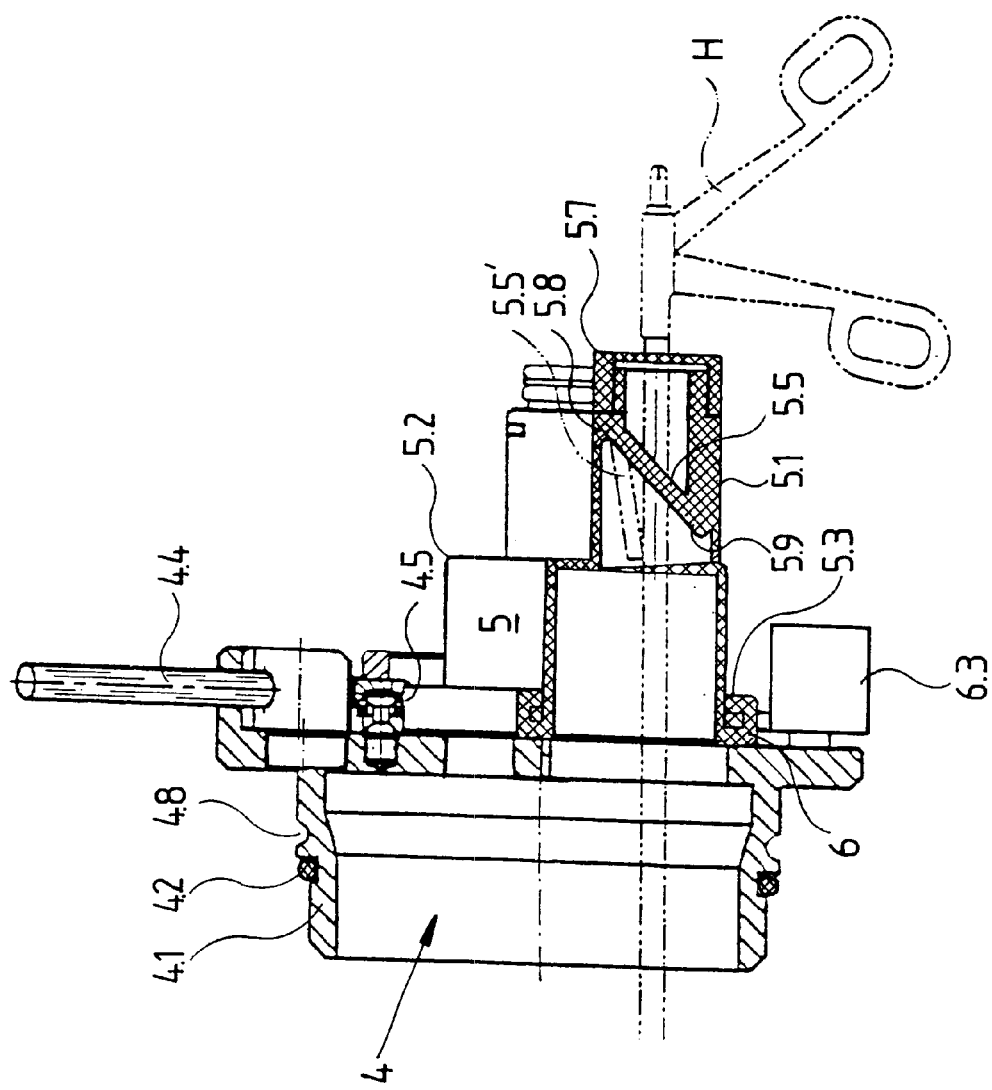
FIG. 2 shows in a sectioned view the carrier with the working insert.

The carrier 4 represented in section in FIG. 2 has a distal-side end 4.1, graduated in diameter, on which there is arranged a sealing ring 4.2 and which for the engagement of the blocking balls 3.6 of the coupling housing 3 comprises an annular groove 4.8. In the upper region of the proximal end-face side of the carrier 4 there is arranged a cylindrical extension 4.3 with a channel (second passage) for leading through the optic O fixable via an eccentric lever 4.4 (not shown in FIG. 2).

Roughly in the region between the eccentric lever 4.4 and the cylindrical extension 4.3 forming the channel there are arranged two fastening pegs 4.5 distanced to one another, whose shape and function for fixing the seal 5 on the carrier 4 will be explained in more detail further below with reference to FIGS. 7 and 8.

With respect to FIGS. 2 to 6 now details of the design of the carrier 4 and the seal 5 will be explained in more detail. In the carrier 4 there is located in the region between the mentioned cylindrical extension 4.3 and the lower end of the carrier 4 an essentially crescent-shaped, relatively large-lumen designed opening 4.7, as a first passage, which may be closed in a gas and fluid-tight manner with the seal 5 using a holder 6 encompassing the seal 5.

The seal 5 comprises a one-piece base body 5.2, formed of elastic material, which is encompassed by the likewise crescent-shaped holder 6 formed as a bow. The base body 5.2 comprises a crescent-shaped attachment 5.3 which is shaped according to the crescent shape of the first passage 4.7, is designed as one piece with the base body 5.2 and which likewise is formed of the same elastic material, whilst the base body 5.2 at its proximal end for example comprises three elastic introduction sockets 5.1 which on the proximal side in each case form a sealing cap 5.7 or are equipped separately with a sealing cap. A valve flap 5.5 closes the inside of the respective socket 5.1 when no auxiliary instrument is inserted.

The valve flap 5.5 according to FIG. 2 closes the passage of the respective introduction socket 5.1 with respect to a proximal through-flow of fluid when no auxiliary instrument is inserted through the introduction socket. Furthermore the valve flap 5.5 consisting of elastic material according to the representation above at 5.8 with an end region lying perpendicular to the instrument longitudinal axis is fixed on the end side in a hinge-like manner. The flap by way of bending at this location is elastically deformed and is brought into a position inclined obliquely distally to the instrument axis and bears with its free end region under a certain spring bias on a valve seat 5.9 running obliquely in the same manner. If an auxiliary instrument is pushed into the introduction socket this with its distal end presses the valve flap 5.5 out of the way, wherein the valve flap is pivoted into the position shown dashed in FIG. 2.

The fixing of the seal 5 on the carrier 4 is effected on the one hand by way of the bow-shaped holder 6 adapted to the outer contour of the base body, in that this holder with its two upper fork-shaped ends 6.1 each having a recess 6.2 engage in and around corresponding circumferential constrictions of the fastening pegs 4.5 of the carrier 4, and on the other hand in that a projection 6.3 located at the lower end of the holder 6 engages behind a lug 4.6 located on the lower part of the proximal side of the carrier 4.

The seal 5 or an annular shoulder located on its distal-side attachment 5.3 is provided with a deepening 5.4 accommodating the holder 6. The seal 5 acts when this annular shoulder 5.3 of the seal 5 is pressed by the holder 6 against the proximal-side end-face side of the carrier 4.

Figure 6:
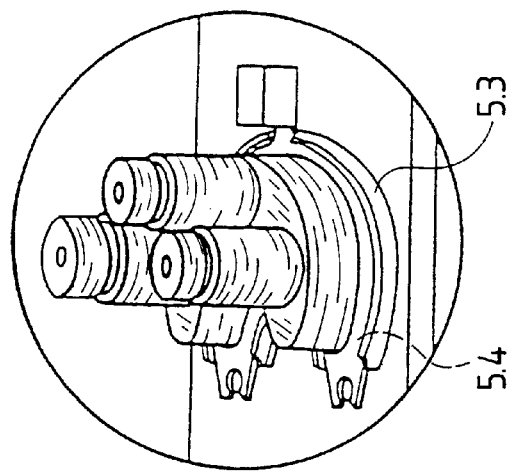
FIGS. 4 to 6 show various stages on inserting the base body into the holder of the seal.
Figure 5:
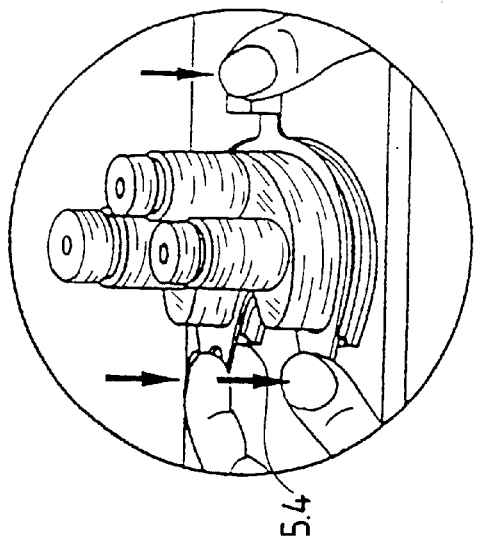
Figure 4:
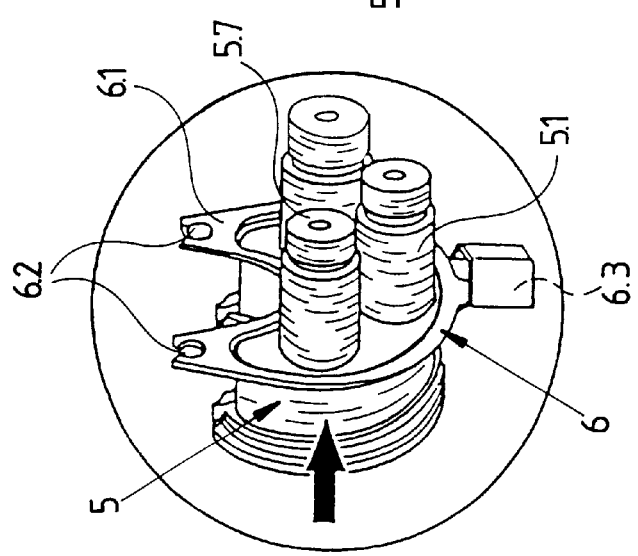

The FIGS. 4 to 6 show in each case in a perspective representation, how the holder 6 firstly from the proximal side is pushed over the base body of the seal 5 (FIG. 4) and finally (FIGS. 5 and 6) is pressed into the deepening 5.4 formed on the proximal side of the annular shoulder of the base body 5.2 so that on the one hand the holder 6 encompasses the base body 5.2 in the region of its attachment 5.3 with a positive fit and on the other hand the crescent-shaped formed deepening 5.4 accommodates the holder 6 with a positive fit and then forms a sealing lip.

Subsequently the complete seal 5 composed of the base body 5.2 and the holder 6 is attached to the proximal end-face side of the carrier 4 (FIG. 7), so that the mentioned recesses 6.2 of the holder 6 may grip around the fastening pegs 4.5.

FIG. 7*a* shows in an enlarged representation the fastening pegs 4.5 of the carrier 4 and the recesses 6.2 of the holder shortly before these may be pressed in the direction indicated by arrows into the circumferential constrictions of the fastening pegs 4.5. With this the cylindrical extension 4.3 and thus the second passage for the optic lie centrally between the bow ends of the holder 6.

By way of the elastic restoring force of the sealing lip, on the annular shoulder, pressed by the holder 6 against the carrier 4 and by way of the centering effect of the peg shanks of this which proximally become larger in diameter in a conical manner, a sealed and secure fastening of the seal on the proximal end-face side of the carrier 4 is achieved. Finally, as shown in FIG. 7, the projection 6.3 on the holder is pressed distally, i.e. to the proximal end-face side of the carrier 4, and with the projection 6.3 engages behind the lug 4.6 formed on the carrier 4, so that the seal 5 latches into its position provided on the carrier 4. The seal 5 may easily be released again from the carrier when the projection 6.3 of the holder 6 is again pressed distally and simultaneously is pivoted somewhat in the clockwise direction as well as when the seal 5 is pulled proximally.

By way of the relatively high friction which the elastic material from which the base body 5.2 is manufactured possesses the security against a lateral displacement of the seal 5 on the carrier 4 is effectively increased. Thus the use of the holder 6 simplifies the fastening and the releasing of the seal to and from the carrier 4 since the holder 6 only needs to be suspended into the fastening pegs 4.5 and with the projection 6.3 pressed against the lug 4.6 formed on the carrier 4.

It is yet to be mentioned that instead of the separate formation of the base body 5.2 and the holder 6 shown in the figures, also a one-piece design of these may be manufactured so that the seal as a whole is one piece and as, a cheap one-way article, after effected use may be disposed of. If one unites the base body 5.2 and the holder 6 with the manufacture of the seal 5 to a single component then also the handling, i.e. the fastening of the seal 5 with the holder 6 on the carrier 4 is advantageously simplified.

Instead of the three sockets 5.1 projecting from the proximal side of the base body 5.2 only two sockets or also only one socket may be provided. It is also conceivable that the socket(s) 5.1 and the sealing caps 5.7 releasably placed on their proximal end, as already mentioned, may be united to a one-piece part.

What is claimed is:

1. A medical instrument, comprising:
   an instrument shank;
   a coupling housing sitting on a proximal side of the instrument shank; and
   a working insert releasably connected to said housing, the insert including a carrier and a seal carried by the carrier, the insert having at least one elastic socket for sealed leading-through of auxiliary instruments and seals a first axial passage formed in the carrier with respect to the coupling housing, the seal having a holder and a base body located in the holder, the seal and the socket forming a one-piece component of elastic material, the holder having means for releasably connecting to the carrier.

2. A medical instrument according to claim 1, wherein the first passage in the carrier has a contour that matches with a contour of a distal-side attachment on the base body of the seal, the socket being arranged to project proximally from the base body so as to open in a passage of the base body in a region of the attachment.

3. A medical instrument according to claim 2, wherein the contour of the first passage and of the attachment on the base body are crescent-shaped.

4. A medical instrument according to claim 3, wherein the holder is bow-shaped and comprises an opening corresponding to the crescent-shaped contour of the attachment of the base body so that the holder encompasses the base body in the region of the attachment.

5. A medical instrument according to claim 4, wherein the carrier has fastening pegs that project proximally from an end-face side of the carrier and taper conically towards the distal side, the ends of the bow-shaped holder in each case comprise a recess so that the end is fork-shaped and releasably fastenable with a positive and non-positive fit on the carrier on the fastening pegs.

6. A medical instrument according to claim 5, wherein a second axial passage is provided in the carrier at a distance from the first passage so that the second passage lies free of the seal.

7. A medical instrument according to claim 6, wherein the fastening pegs lie symmetrically to the second passage and at both sides of the second passage.

8. A medical instrument according to claim 2, wherein the holder is substantially crescent-shaped and lies on an annular shoulder formed on the distal-side attachment of the base body.

9. A medical instrument according to claim 8, wherein a proximal-side surface of the annular shoulder comprises a crescent-shaped depression that accommodates the holder with a positive fit and forms a reinforcement for a sealing lip which represents a contact surface between the seal the carrier.

10. A medical instrument according to claim 1, wherein the instrument shank is releasably fastened on the coupling housing.

11. A medical instrument according to claim 1, and further comprising a handle connected to the coupling housing so as to have a free end that projects from the coupling housing, and fastening means provided at the free end of the handle for fastening on a mounting.

12. A medical instrument according to claim 1, wherein three sockets are provided on the base body.

13. A medical instrument according to claim 1, wherein the holder is made of metal.

14. A medical instrument according to claim 1, wherein the holder is plastic.

15. A medical instrument according to claim 1, wherein the holder and the base body form a single component.

16. A medical instrument according to claim 15, wherein the single component formed of the holder and of the base body is a one-way usage article.

17. A medical instrument according to claim 1, and further comprising a pivotable valve flap which distally and with respect to a instrument longitudinal axis runs inclined, is fixed on one side in the socket and with its free end region lies against a valve seat running inclined in a common manner, so that a passage of the socket is blockable by the valve flap.

* * * * *